(12) United States Patent
Petricoin, III et al.

(10) Patent No.: US 8,834,873 B2
(45) Date of Patent: Sep. 16, 2014

(54) METHOD FOR DETECTING AND CONTROLLING CANCER

(75) Inventors: Emanuel F. Petricoin, III, Gainesville, VA (US); Mariaelena Pierobon, Fairfax, VA (US); Valerie Calvert, Arlington, VA (US); Lance A. Liotta, Bethesda, MD (US)

(73) Assignees: George Mason Research Foundation, Inc., Fairfax, VA (US); Istituto Superiore di Sanita, Rome (IT)

( * ) Notice: Subject to any disclaimer, the term of this patent is extended or adjusted under 35 U.S.C. 154(b) by 411 days.

(21) Appl. No.: 12/513,040

(22) PCT Filed: Oct. 31, 2007

(86) PCT No.: PCT/US2007/022863
§ 371 (c)(1),
(2), (4) Date: Apr. 30, 2009

(87) PCT Pub. No.: WO2008/057329
PCT Pub. Date: May 15, 2008

(65) Prior Publication Data
US 2010/0074895 A1    Mar. 25, 2010

Related U.S. Application Data

(60) Provisional application No. 60/855,751, filed on Nov. 1, 2006.

(51) Int. Cl.
*A61K 39/395* (2006.01)
*C07K 16/22* (2006.01)
*G01N 33/574* (2006.01)

(52) U.S. Cl.
CPC .......... *C07K 16/22* (2013.01); *G01N 33/57438* (2013.01)
USPC ....................................... 424/133.1

(58) Field of Classification Search
None
See application file for complete search history.

(56) References Cited

U.S. PATENT DOCUMENTS

| | | |
|---|---|---|
| 8,628,931 B2 | 1/2014 | Liotta et al. |
| 2006/0019280 A1 | 1/2006 | Chen et al. |
| 2006/0182751 A1 | 8/2006 | Gazzard et al. |
| 2006/0216288 A1 | 9/2006 | Chang et al. |
| 2007/0166388 A1* | 7/2007 | Desai et al. ............ 424/489 |
| 2008/0255243 A1* | 10/2008 | Petricoin et al. ........... 514/648 |
| 2010/0003247 A1 | 1/2010 | Petricoin et al. |

FOREIGN PATENT DOCUMENTS

WO    WO 2007/106432 A2    9/2007

OTHER PUBLICATIONS

Rutkowski et al Neoplasma vol. 50 p. 438 (2003).*
Reddy et al Clinic in colon and rectal surgery (May 2006) vol. 19 p. 69.*
Hirota et al Science vol. 279 p. 577 (1998.*
Supplementary European Search Report for European Application No. EP 07 86 7299, dated Dec. 17, 2010.
C. Belluco, et al., "Kinase substrate protein microarray analysis of human colon cancer and hepatic metastasis." Clinica Chimica Acta. Elsevier BV. Amsterdam, NL, vol. 357, No. 2, Jul. 24, 2005, pp. 180-183.
V. Espina, et al., "Pathology of the Future: Molecular Profiling for Targeted Therapy," Cancer Investigation, 1:36-46, 2005.
R. Grubb, et al., "Signal Pathway Profiling of Prostate Cancer Using Reverse Phase Protein Arrays," Proteomics, Wiley—VCH Verlag, Weinheim, DE, vol. 3, No. 11, Nov. 1, 2003, pp. 2142-2146.
E. Petricoin, et al., "Mapping molecular networks using proteomics: a vision for patient-tailored combination therapy", Journal of Clinical Oncology. American Society of Clinical Oncology, US., vol. 23, No. 15, May 20, 2005, pp. 3614-3621.
K. Sheenan, et al., "Use of reverse phase protein microarrays and reference standard development for molecular network analysis of metastatic ovarian carcinoma", Molecular & Cellular Proteomics. American Society for Biochemistry and Molecular Biology, Inc., US, vol. 4, No. 4, Apr. 1, 2005 pp. 346-355
J. Wulfkuhle, et al., "Genomic and proteomic technologies for individualisation and improvement of cancer treatment," European Journal of Cancer 40 (2004) 2623-2632.
J. Wulfkuhle, et al., "Technology insight: pharmacoproteomics for cancer—promises of patient-tailored medicine using protein microarrays," Nature Clinical Practice Oncology. Nature Publishing Group, vol. 3, No. 5, May 1, 2006, pp. 256-268.
Heymach, et al., "Epidermal Growth Factor Receptor Inhibitors in Development for the Treatment of Non-Small Cell Lung Cancer", *Clinical Cancer Research*, 2006, vol. 12, No. 14, pp. 4441s-4445s.
LaCouture, et al., "Cutaneous reaction to anticancer agents targeting the epidermal grown factor receptor: a dermatology-oncology prespective" abstract, *Skin Therapy, Letter*, Database Medline on STN No. 2007540822, (2007).
Tsurutani, J., et al., "Inhibition of the Phosphatidylinostol 3-Kinase/Akt/Mammalian Target of Rapamycin Pathway but not the MEK/ERK Pathway Attenuatese Lamin-Mediated Small Cell Lung Cancer Cellular Survival and Resistance to Imatinib Mesylate of Chemotheraphy", Cancer Res 2005, vol. 65, No. 18, pp. 8423-8432.
International Search Report for International Application PCT/US2007/022863, dated Jul. 8, 2008. (3 pgs.).

* cited by examiner

*Primary Examiner* — Sheela J Huff
(74) *Attorney, Agent, or Firm* — Geoffrey M. Karny (57) ABSTRACT

Methods are provided for treating cancer metastasis by administering a therapeutic composition targeting a kinase substrate cascade.

31 Claims, 5 Drawing Sheets

METHOD FOR DETECTING AND CONTROLLING CANCER

CROSS-REFERENCE TO RELATED APPLICATIONS

This application claims priority to U.S. Provisional Application No. 60/855,751, filed Nov. 1, 2006, which is hereby incorporated by reference.

BACKGROUND

Cancer is a complex and devastating group of diseases that kills one in five adults in developing countries. Although cancers arise from a wide variety of cells and tissues in the body, there are unifying features of this group of diseases. Cancer is predominantly a genetic disease, resulting from the accumulation of mutations that promote clonal selection of cells that exhibit uncontrolled growth and division. The result of such uncontrolled growth of tumor cells is the formation of disorganized tissue that compromises the function of normal organs, ultimately threatening the life of a patient.

Basic research designed to unravel the mechanics of carcinogenesis have revolutionized our understanding of the molecular nature of genetic changes that initiate tumor formation. Notably, specific genes have been identified that are frequently mutated in tumor cells. These genes regulate, for example, DNA damage repair, homologous recombination, cell cycle control, growth factor signaling, apoptosis, differentiation, angiogenesis, immune response, cell migration, and telomere maintenance. Thus, based on mutations in certain genes, it is possible to distinguish cancer cells from normal cells.

However, despite advances in our understanding of the genetic basis underlying cancer cell phenotypes, effective methods for treating cancer remain largely undiscovered. While chemotherapeutic agents are designed to kill or block tumor cell proliferation, chemotherapeutic agents are frequently unable to exclusively suppress upregulated activity of a particular protein in a tumor cell without deleteriously affecting necessary levels of protein activity in normal cells. In the case of metastasized cancer, current cancer treatments, such as chemotherapy and radiation, are generally ineffective.

SUMMARY

In one aspect, the invention provides a method of treating a patient with liver metastasis, comprising administering to the patient an effective amount of at least one therapeutic selected from the group consisting of GLEEVEC, AVASTIN, TARCEVA, VECTIBIX, and Lapatinib.

In one embodiment, the therapeutic is GLEEVEC. In another embodiment, the therapeutic is AVASTIN. In another embodiment, the therapeutic is TARCEVA. In another embodiment, the therapeutic is Lapatinib. In another embodiment, the therapeutic is VECTIBIX. In another embodiment, the therapeutic is GLEEVEC and AVASTIN. In another embodiment, the therapeutic is AVASTIN and TARCEVA. In another embodiment, the therapeutic is TARCEVA and Lapatinib. In another embodiment, the therapeutic is GLEEVEC and TARCEVA. In another embodiment, the therapeutic is GLEEVEC and Lapatinib. In another embodiment, the therapeutic is GLEEVEC and VECTIBIX. In another embodiment, the therapeutic is AVASTIN and Lapatinib.

In another embodiment, the method may further comprise (a) procuring a biopsy from the patient; (b) subjecting the biopsy to epithelial cell enrichment; (c) lysing the epithelal cells to produce a lysate; (d) analyzing the lysate by immunoassay, wherein the immunoassay is selected from the group consisting of an ELISA, reverse phase array, suspension bean array, and immunohistochemical detection; (e) comparing the intensity value to a high and low reference value; and (f) reporting the value to a physician.

In another aspect, the invention provides a method of treating a patient with pulmonary metastasis, comprising administering to the patient an effective amount of at least one therapeutic selected from the group consisting of GLEEVEC, AVASTIN, TARCEVA, VECTIBIX, and Lapatinib.

In one embodiment, the therapeutic is GLEEVEC. In another embodiment, the therapeutic is AVASTIN. In another embodiment, the therapeutic is TARCEVA. In another embodiment, the therapeutic is Lapatinib. In another embodiment, the therapeutic is VECTIBIX. In another embodiment, the therapeutic is GLEEVEC and AVASTIN. In another embodiment, the therapeutic is AVASTIN and TARCEVA. In another embodiment, the therapeutic is TARCEVA and Lapatinib. In another embodiment, the therapeutic is GLEEVEC and TARCEVA. In another embodiment, the therapeutic is GLEEVEC and Lapatinib. In another embodiment, the therapeutic is GLEEVEC and VECTIBIX. In another embodiment, the therapeutic is AVASTIN and Lapatinib.

In one aspect, the invention provides a method of treating a patient with liver metastasis, comprising administering to the patient an effective amount of an akt inhibitor.

In another aspect, the invention provides a method of treating a patient with pulmonary metastasis, comprising administering to the patient an effective amount of an akt inhibitor.

In another aspect, the invention provides a method of treating a patient with liver metastasis, comprising administering to the patient an effective amount of a PI3kinase inhibitor.

In another aspect, the invention provides a method of treating a patient with pulmonary metastasis, comprising administering to the patient an effective amount of a PI3kinase inhibitor.

In another aspect, the invention provides a method of treating a patient with liver metastasis, comprising administering to the patient an effective amount of an akt inhibitor and at least one of GLEEVEC, AVASTIN, TARCEVA, VECTIBIX, and Lapatinib.

In another aspect, the invention provides a method of treating a patient with pulmonary metastasis, comprising administering to the patient an effective amount of an akt inhibitor and at least one of GLEEVEC, AVASTIN, TARCEVA, VECTIBIX, and Lapatinib.

Other objects, features and advantages will become apparent from the following detailed description. The detailed description and specific examples are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

DETAILED DESCRIPTION

Mapping tumor cell protein networks revealed altered signaling pathways in cancer progression. In particular, network analysis of expected kinase substrate cascades revealed differences between primary and metastatic lesions. Moreover, the elevated phosphorylation events fell into only a few major signaling pathways, known to be involved in pro-survival, growth receptor and motility related events. Targeting the associated kinases would disrupt aberrant signal pathways and thwart metastasis. Thus, methods for treating liver or lung metastasis involve administering therapeutics that target the c-kit, PDGFr, abl family of kinases, the VEGFr family of kinases, the EGFr family of kinases and the AKT/mTOR pathway.

Metastasis refers to a complex series of steps in which cancer cells migrate from the original tumor site to other parts of the body via the bloodstream or lymph system. In doing so, malignant cells detach from the primary tumor and attach to and degrade proteins comprising the surrounding extracellular matrix (ECM), which separates the tumor from adjoining tissue. By degrading these proteins, cancer cells are able to breach the ECM and migrate.

The most common places for the metastases to occur are the adrenals, liver, brain, and the bones. There is also a propensity for certain tumors to seed in particular organs. For example, prostate cancer usually metastasizes to the bones. Similarly, colon cancer has a tendency to metastasize to the liver. Stomach cancer often metastasizes to the ovary in women, where it forms a Krukenberg tumor.

It is this ability to migrate or metastasize to other tissues and organs that makes cancer a potentially life-threatening disease. Accordingly, the present invention provides methods for treating cancer metastasis.

The present invention uses terms and phrases that are well known to those practicing the art. Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described herein are those well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology (Molecular Cloning, A Laboratory Manual, 3rd. edition, edited by Sambrook & Russel Cold Spring Harbor Laboratory Press, Cold Spring Harbor, N.Y., 2001).

I. Mapping Tumor Cell Networks

The sequencing of the human genome prompted a revolution in technologies that facilitate molecular profiling in disease research. In the field of oncology, for example, array technologies have been used for profiling tumors at the DNA, RNA, and protein levels. Protein microarrays provide an especially powerful technology for drug discovery, biomarker identification, and signal transduction profiling of cellular material. Specifically, and as contemplated in the present invention, protein microarrays can be used for profiling cellular signaling pathways by monitoring changes in phosphorylation over time, for example, before and after a particular treatment, between disease and non-disease states, and between responders and nonresponders. Reviewed in Wulfkuhle, J. et al. *Nat Clin Pract Oncol.* 3:5:256-68 (2006), which is hereby incorporated by reference in its entirety. Based on protein phosphorylation activities, particular pathways can be identified and used for tailoring patient-specific treatment. Liotta, L. *Cancer Cell* 3:317-325 (2003), which is hereby incorporated by reference in its entirety.

Protein microarrays are classified depending on whether the analytes are captured from solution phase or bound to the solid phase. In forward-phase arrays (FPAs), the capture molecules are immobilized onto the substratum and act as a bait molecule. In contrast, reverse-phase arrays (RPAs) immobilize an individual test sample in each array spot such that an array is comprised of hundreds of different samples. Because human tissues comprise hundreds of interacting cell populations, RPAs afford the ability to identify changes in the cellular proteome. Methods for preparing protein microarrays are routine and well-known in the art and are disclosed, for example, in Nishizuka, S. et al. *Proc Natl Acad Sci USA* 100: 14299:14234; Paweletz et al. *Oncogene* 20:1981-1989 (2001).

Based on changes in phosphorylation levels, it is possible to identify signaling pathways that are known to be involved in pro-survival, growth receptor, and motility related events. Targeting the associated kinases disrupt aberrant signal pathways and thereby thwart metastasis. Accordingly, methods for treating liver or lung metastasis involve administering therapeutics that target the c-kit, PDGFr, abl family of kinases, the VEGFr family of kinases, the EGFr family of kinases, and the AKT/mTOR pathway.

II. Therapeutics for Targeting Kinase Pathways

There are several known and readily available drugs that can be used for targeting a kinase pathway and thereby used as a means for treating metastasized cancer, such as liver or lung metsastasis.

Imatinib mesylate, also called Gleevec® or STI571, is approved by the U.S. Food and Drug Administration (FDA) for the treatment of some forms of adult and pediatric chronic myelogenous leukemia (CML), and for the treatment of a rare form of cancer called gastrointestinal stromal tumor (GIST). Gleevec® is the first approved drug to directly turn off the signal of a protein known to cause a cancer. Gleevec® inhibits the receptor tyrosine kinases for platelet-derived growth factor (PDGF) and stem cell factor (SCF)/c-kit; the SCF/c-kit receptor tyrosine kinase. Other molecular-targeting drugs previously approved by the FDA interfere with proteins associated with other cancers, but not with proteins that directly cause the disease.

Avastin®, or Bevacizumab, is approved by the FDA for use with other drugs to treat colorectal cancer that has spread to other parts of the body. Avastin® is also approved for use with other drugs to treat non-small cell lung cancer that cannot be removed by surgery, has spread to other parts of the body, or has recurred. Avastin® is a recombinant humanized monoclonal antibody directed against the vascular endothelial growth factor (VEGF), a pro-angiogenic cytokine. Avastin® binds to VEGF and inhibits VEGF receptor binding, thereby preventing the growth and maintenance of tumor blood vessels.

Tarceva®, also known as erlotinib hydrochloride or N-(3-Ethynylphenyl)-6,7-bis(2-methoxyethoxy)-4-quinazolinamine Monohydrochloride, is approved by the FDA for treating forms of non-small cell lung cancer that have not responded well with chemotherapy. Competing with adenosine triphosphate, Tarceva® reversibly binds to the intracellular catalytic domain of epidermal growth factor receptor (EGFR) tyrosine kinase, thereby reversibly inhibiting EGFR phosphorylation and blocking the signal transduction events and tumorigenic effects associated with EGFR activation.

Lapatinib (Tykerb®) is an experimental drug that blocks the activity of the HER2 protein, a protein frequently found in breast cancers. Tumors that overexpress HER2 (called HER2-positive) tend to grow faster and are more likely to come back than tumors that don't overexpress the protein. Lapatinib binds to the part of the HER2 protein found inside breast cancer cells.

Several signaling pathway inhibitors are known and can be used as a cancer metastasis therapeutic. Such inhibitors include but are not limited to akt and PI3kinase inhibitors.

III. Administering Therapeutics

Each therapeutic drug, or a combination of drugs, may be administered by a variety of methods. As used herein, therapeutic drug includes proteins, such as antibodies, and small molecules. For effective treatment, the present invention contemplates administering each drug, either alone or in combination with another drug, by topical, oral, anal, ocular, buccal, nasal, intramuscular, subcutaneous, intravenous, or parenteral routes. The ultimate choice of route, formulation, and dose is made by the attending physician and is based upon a patient's unique condition.

Where the administration is by bolus injection, including bolus injection of a slow release formulation, dosing schedules also can be continuous in that the drug is administered each day, or may be discontinuous. Discontinuous bolus injection dosing schedules, for example, include on periods (days on which an injection is given) selected from 1, 2, 3, 4, 5, 6, or 7 days, 1, 2, 3, 4, or more weeks, or any combination thereof, and off periods (days on which an injection is not given) selected from 1, 2, 3, 4, 5, 6, or 7 days, 1, 2, 3, 4, or more weeks.

As will be apparent to one of skill in the art, intranasal and inhalant administration is generally more convenient for the subject as it does not involve the use of injections, catheters or transdermal infusion devices. Intranasal and inhaled doses may thus be smaller, but given more frequently, than doses given by other parenteral routes. Accordingly, intranasal and inhalant dosing schedules can include a single dose per "on" day, or can involve multiple doses (e.g., 2, 3, 4, 5 or more doses per day). Dosing schedules may be continuous or discontinuous, with discontinuous schedules utilizing on periods (e.g., days on which the drug is administered at least once) selected from 1, 2, 3, 4, 5, 6, or 7 days, 1, 2, 3, 4, or more weeks, or any combination thereof, and off periods (e.g., days on which the drug is not administered) selected from 1, 2, 3, 4, 5, 6, or 7 days, 1, 2, 3, 4, or more weeks.

Continuous and discontinuous administration schedules by any method also include dosing schedules in which the dose is modulated throughout the "on" period, such that, for example, at the beginning of the on period, the dose is low and increased until the end of the on period, the dose is initially high and decreased during the on period, the dose is initially low, increased to a peak level, then reduced towards the end of the on period, and any combination thereof.

A drug, or combination thereof, may be administered by parenteral route such as, but not limited to, intravenous (IV), intramuscular (IM), subcutaneous (SC), intraperitoneal (IP), transdermal, intranasal, and inhalant routes. IV, IM, SC, and IP administration can be by bolus injection or bolus infusion or continuous infusion, and in the case of SC or IM, also can be by slow release implantable device, including, but not limited to, pumps, slow release formulations and mechanical devices. For example, the invention contemplates administering at least one of GLEEVEC, AVASTIN, TARCEVA, Lapatinib, which of course allows various drug combinations.

In general, a dose that is administered by subcutaneous or intramuscular injection will be greater than the therapeutically-equivalent dose given intravenously. Preferably, the drug is dissolved in physiologically compatible carriers such as normal saline, or phosphate buffered saline solution.

For potential administration, compositions of the drug may be semi-solid or liquid preparations, such as liquids, suspensions, and the like. Physiologically compatible carriers include, but are not limited to, normal saline, serum albumin, 5% dextrose, and plasma preparations. For intranasal and inhalant administration, a powdered formulation, such as a freeze-dried powder, may be useful. Optionally, the carrier also can include anti-microbial agents, preservatives, detergents, or surfactants.

A "therapeutically effective" amount may be determined by prevention or amelioration of adverse conditions or symptoms of diseases, injuries, or disorders being treated. In the context of the present invention, a "therapeutically effective" amount would reduce metastasis in liver and lung tissues. The dose of a particular drug to be administered can be determined readily by those skilled in the art, based on the condition to be treated, the severity of the condition, the type of cytotoxic agent or radiation used, and the patient's medical history. Preferably, when the drug is administered daily, the subcutaneous or intramuscular dose for a human is about 0.05 mg/kg to 50 mg/kg of body weight per day. More preferably, the daily subcutaneous or intramuscular dose for a human is about 0.5 mg/kg to 20 mg/kg. Most preferably, the daily subcutaneous or intramuscular dose for a human is about 0.5 mg/kg to 5 mg/kg. For subcutaneous or intramuscular administration, the dose is preferably greater than the therapeutically equivalent dose given intravenously.

For example, the FDA recommended dosage of Gleevec is 400 mg per day for patients in chronic phase CML and 600 mg per day for patients in accelerated phase or blast crisis. Based on these guidelines, and depending on the severity of the cancer metastasis and the health of the patient, the dosage could be 400-420, 420-440, 440-460, 460-480, 480-500, 500-520, 520-540, 540-560, 560-580, and 580-600 mg per day. The prescribed dose should be administered orally, once daily with a meal and a large glass of water. Treatment should be continued as long as the patient continues to benefit. The formulation, route and method of administration, and dosage will depend on the medical history of the patient, including the severity of the disease.

A therapeutic drug can be combined with another drug, along with inert pharmaceutical excipients such as lactose, oil, mannitol, and starch to form pharmaceutical compositions. Such compositions can be formulated into dosage forms such as elixirs, liquids, ointments, lotions, IV fluids, alcohol, tablets, capsules, and the like. For parenteral, intramuscular, subcutaneous and intravenous administration, a drug can be formulated with an inert, parenterally acceptable vehicle such as water, saline, sesame oil, ethanol buffered aqueous medium, propylene glycol and the like. For topical and oral administration, a drug can be formulated with waxes, oils, buffered aqueous medium, and the like. These various pharmaceutical dosage forms are compounded by methods well-known in the art.

The drugs of the present invention also can be prepared as pharmaceutically acceptable salts. A pharmaceutically acceptable salt means a salt formed between any one or more of the charged groups in a peptide and any one or more pharmaceutically acceptable, non-toxic cations or anions.

Organic and inorganic salts include, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, carbonic, and the like. Pharmaceutically acceptable salts may also contain cations including, but not limited to, ammonium, sodium, potassium, calcium, or magnesium.

Specific examples are presented below for controlling cancer metastasis. They are meant to be exemplary and not as limitations on the present invention.

EXAMPLES

Example 1

Mapping Tumor Cell Networks

Using laser capture microdissection, 68 cases of patient-matched (from 34 patients) colorectal cancer and hepatic metastasis and 15 cases of pulmonary metastasis from the colon were obtained. Pure cancer cell populations were lysed and subjected to reverse-phase protein microarray technology as described in Petricoin, E. et al. *J Clin Oncol*, 23:15: 3614-20 (2003) and incorporated by reference in its entirety.

Using this technique, the phosphorylation state of 70 kinase substrates were measured and molecular network analysis was performed using commercially available software (Microvigene, VigeneTech, MA). Of the 70 phosphoendpoints analyzed, 21 were statistically significant (Student t-test p<0.05) and were expressed between the patient matched colorectal signature and the hepatic metastasis.

Figure 1:
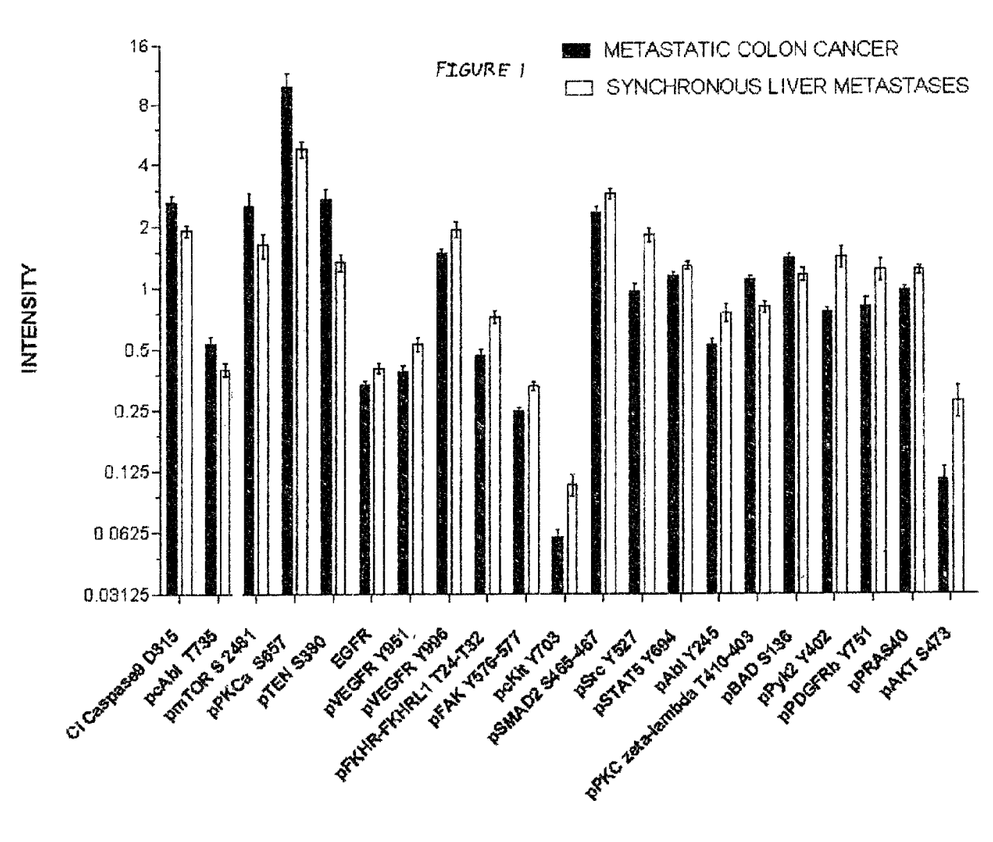
FIG. 1 shows phosphoendpoints differentially elevated in liver metastasis compared with the primary colon.

As shown in FIG. 1, of the 21 statistically significant phosphoendpoints, 14 were elevated in liver metastasis compared with the primary colon. Unexpectedly, the 14 phosphorylation events fell into only a few major signaling pathways. These pathways are known to be involved in pro-survival, growth receptor, and motility related events, and many of which are drug targets for specific targeted therapies.

Moreover, these endpoints nucleated into well-known pathways whereby levels of proteins that are known to be antagonists of the signaling were also predictably down-regulated in liver metastasis. This critical observation provides a large degree of confidence in the final data insofar as entire pathways have been discovered to be deranged. For example, up-regulating a growth factor receptor (i.e. GLEEVEC, AVASTIN, and TARCEVA targets) concomitant with up-regulating downstream prosurvival components pAK, pRAS, FKHRL, STAT5, pSRC, and down-regulation of the tumor suppressor pTEN (controls AKT activity), cleaved caspase 9 and BAD phosphorylation (controls apoptosis) as well as down-regulating PKCalpha and zet-lambda (both shown to modulate AKT activation) were all observed, and were entirely contained within the statistically significant endpoints.

Figure 2:
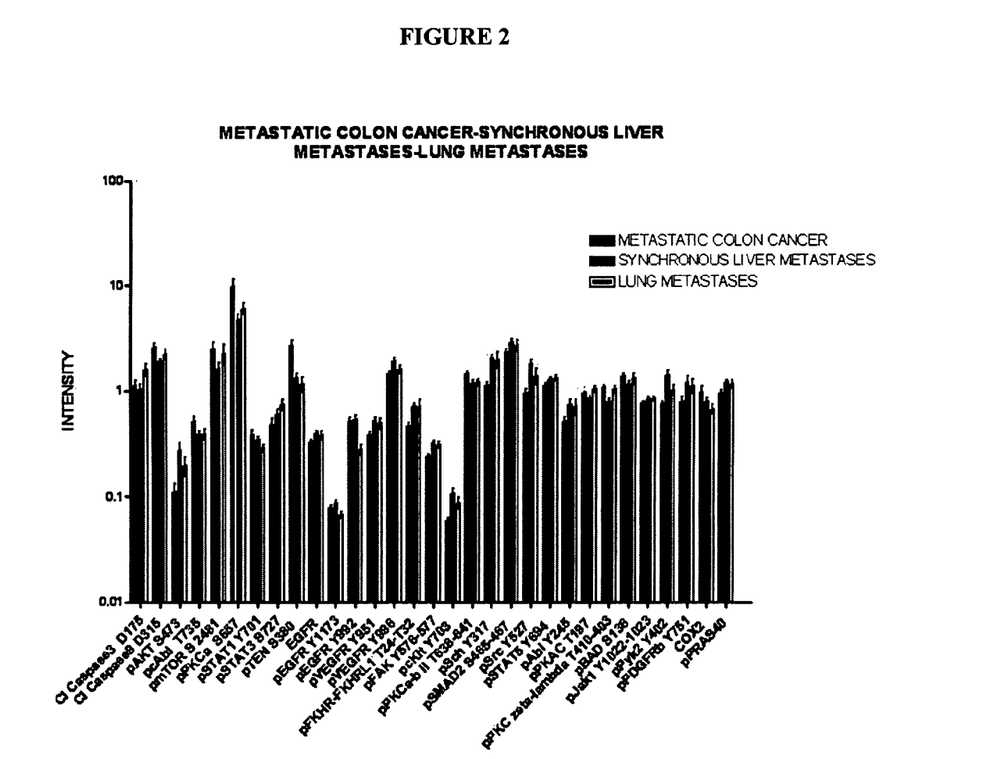
FIG. 2 shows elevated drug targets and pathways observed in colorectal carcinoma that metastasized to the lung.

Furthermore, and as shown in FIG. 2, elevated drug targets and pathways were also observed in colorectal carcinoma that metastasized to the lung, indicating that these pathways could be targeted in both liver and pulmonary metastasis.

Figure 3:
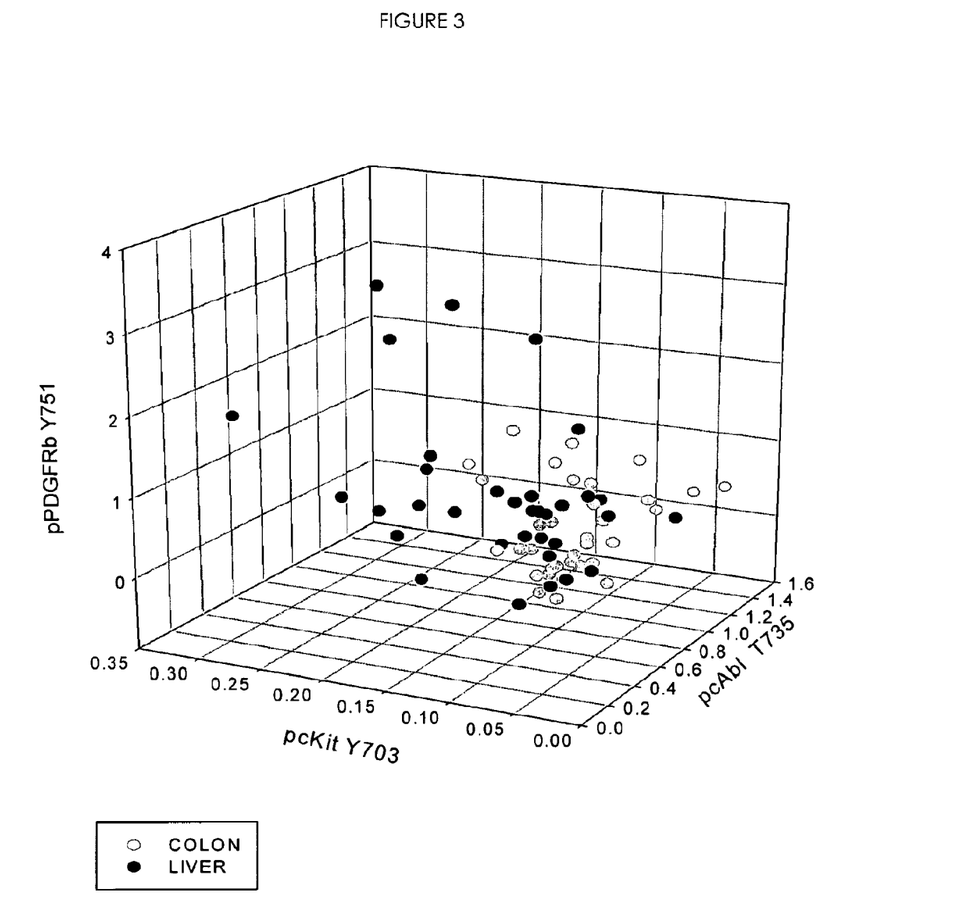
FIG. 3 depicts phosphorylation of pTEN and phospho akt.

FIG. 3 provides a two-way plot using two of the evaluated phosphoendpoints from FIG. 1. In measuring the phosphorylation of pTEN, which regulates akt, and phospho akt, it demonstrates activation of the signaling cascade. When pTEN is phosphorylated, it becomes destabilized and degraded, which prompts akt phosphorylation. From these data, it is apparent that the signaling pathway is dysregulated and in doing so, a cancer cell in the liver would selectively die, thereby thwarting metastasis.

Figure 4:
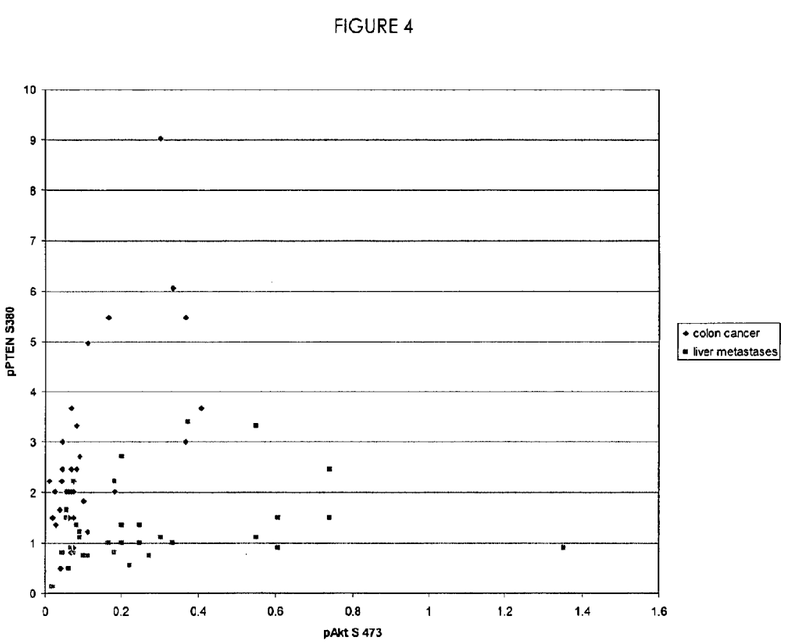
FIG. 4 provides a three-way map of GLEEVEC® targets.

FIG. 4 provides a three-way map for three GLEEVEC targets, each of which are independently activated, thereby providing evidence that dysregulation of a signaling pathway activates cell death.

Example 2

Selecting and Stratifying Patients for Treatment

A predefined cut-value of combined PDGFr/c-kit and c-abl phosphorylation levels (normalized and compared to A431+/−EGF reference material), herein referred to as phospho-Gleevec drug target score (PGDT) can be obtained and used to select and stratify patients for Gleevec therapy. The PGDT is determined by the combination of the phosphorylation of c-abl, c-kit and PDGFr for each patient. The relative phosphorylation of each has been determined based on a reference standard, A431 cells treated with 100 ng/ml EGF for 15 minutes, that is printed and quantified on every assay. The inter and intra assay CV for the PGDT of the A431+EGF reference material was less than 5%, well within clinical diagnostic standard analyte testing determinant, and within our previously published results (Paweletz et al, Oncogene, 2001).

Figure 5:
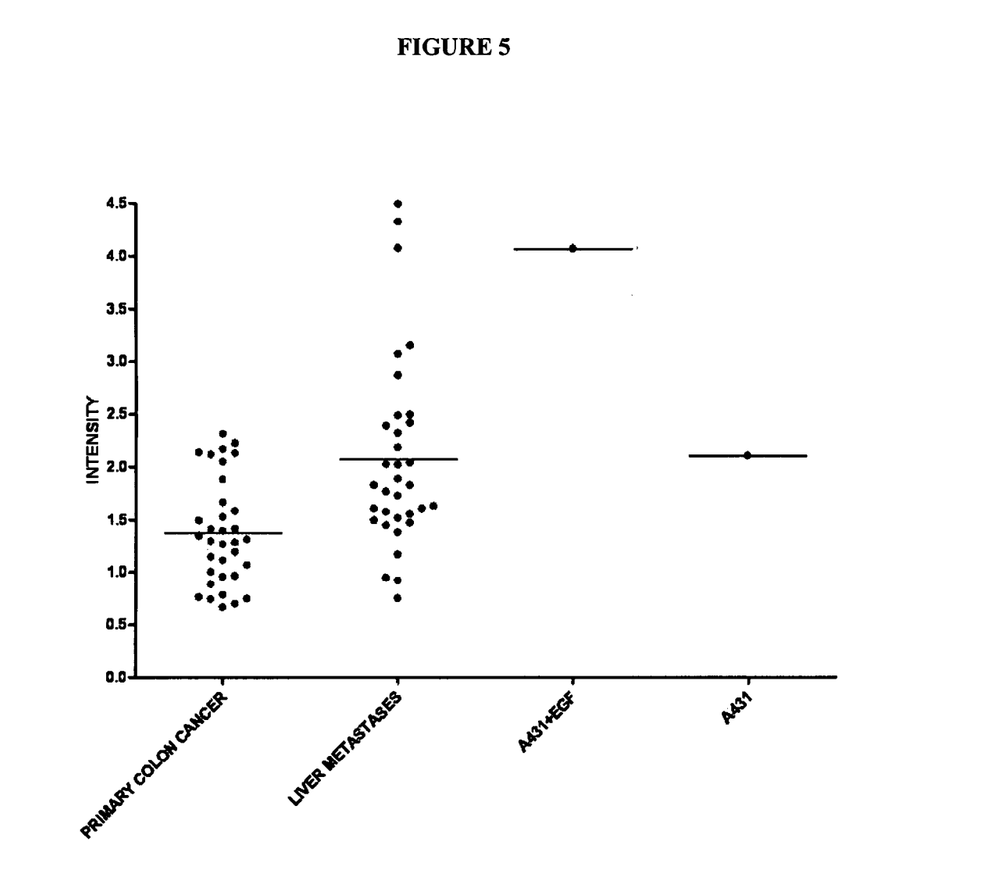
FIG. 5 shows a scatter plot of patient values.

For example, a 28 day run using Gleevec alone prior to administration of panitumumab may be used. Based on preliminary data, a PGDT cut-point of 2.3 relative intensity units (RIU) may be used, since this value would provide 100% specificity: the rationale being that 0/34 primary colorectal cancers would have a value above this cut-point (P<0.00001), as shown below in FIG. 5. A PGDT cut point of 2.3 RIU theoretically would have stratified the top third of all patients within the study set (11/34 patients (33%)). Based on the highly statistical significance of the separation obtained between primary and metastatic disease, it is likely that one-third of the enrollment population will be eligible for the Gleevec arm of the study. Importantly, a PGDT of 2.3 corresponds to a value slightly higher than the average of quintuplicate replicates of the A431 control cell values (2.15+/−0.09). A431 cells are well known to have extraordinarily high EGFR levels and fairly high constitutive signaling in the absence of EGF ligand. Thus, the data provide evidence that using a 2.3 cut-point can be used to select those patients whose metastatic signaling is above the highest signal from any of the primary colorectal cancer levels and higher than the unstimulated A431 cell line.

Example 3

GLEEVEC+Vectibix Treatment

GLEEVEC either alone or in combination with VECTIBIX (Panitumumab) may be effective in the treatment of metastatic colorectal cancer as measured by reduction in tumor size by imaging of the hepatic metastasis. Additionally, GLEEVEC and VECTIBIX efficacy may correlate with phosphorylation levels of PDGFr (Y751), cKIT (Y703), cAbl (Y245), AKT (S473), AKT (T308), mTOR (S2448), mTOR (S2481), 4EBP1 (S65), 4EBP1 (T37/46), 4EBP1 (T70), total EGFR, phospho EGFR (Y1173, Y1068, Y1045, Y845, Y992) using liver biopsy specimens obtained before and after therapy.

For example, patients with a PGDT score ≥2.3, as defined above in Example 2, will receive GLEEVEC monotherapy for a 28 day period with a second biopsy on around day 28. Thereafter, all patients will receive a combination of GLEEVEC and VECTIBIX (6 mg/kg). For patients with PGDT Score <2.3, each patient will receive standard of care therapy (VECTIBIX containing regimen per investigator's discretion). All protein determinants will be measured using reverse phase protein microarray (RPMA) as described above in Example 1.

TABLE 1

Clinical characterization of the 34 matched patients affected by colorectal cancer nd synchronous liver metastases and the 16 cases of metachronous lung metastases from colorectal cancer.

| METASTATIC COLON CANCER MATCHED SYNCHRONOUS LIVER METASTASES | MALE | FEMALE | TOTAL |
|---|---|---|---|
| NUMBER OF PATIENTS: | 21 | 13 | 34 |
| MEDIAN AGE: | 59.8 | 57.07 | |
| YEARS (RANGE): | 37-84 | 33-66 | |
| STAGE: | | | |
| IV-DUKES STAGE D | 21 | 13 | 34 |

| SIT OF THE PRIMARY TUMOR | TOTAL |
|---|---|
| CAECUM/ASCENDING | 4 |
| TRANSVERSE | 1 |
| DESCENDING/SIGMOID | 10 |
| RECTUM | 18 |
| UNKNOWN | 1 |

Table 1 provides data describing the study set sample, which represents a typical population distribution for patients with colorectal cancer that had metastasized to the liver.

TABLE 2

Sample study of patients with lung cancer that has metastasized to the liver.

| LUNG METASTASES FROM COLON CANCER | MALE | FEMALE | TOTAL |
|---|---|---|---|
| NUMBER OF PATIENTS: | 6 | 10 | 16 |
| MEDIAN AGE: | 60.7 | 53 | |
| YEARS (RANGE): | 40-74 | 27-74 | |

Table 2 provides data describing the study set sample, which represents a typical population distribution for patients with lung cancer that had metastasized to the liver.

TABLE 3

Statistically significant endpoints between primary colorectal cancer and synchronous liver metastases.

| VARIABLE | P VALUE | TREND IN THE LIVER METASTASES |
|---|---|---|
| Cl Caspase9 D315 | 0.0066 | ↓ |
| EGFR | 0.0019 | ↑ |
| p4EBP1 S65 | 0.0326 | ↑ |
| pAbl Y245 | 0.0037 | ↑ |
| pAKT S473 | 0.0001 | ↑ |
| pAKT T308 | 0.0163 | ↑ |
| pBAD S136 | 0.0087 | ↓ |
| pcAbl T735 | 0.0251 | ↓ |
| pcKit Y703 | 0.005 | ↑ |
| pEGFR Y 1448 | 0.0424 | ↓ |
| peIF4G S1108 | 0.0416 | ↑ |
| peNOS S1177 | 0.0476 | ↑ |
| pFADDS194 | 0.0222 | ↑ |
| pFAK Y576-577 | 0.0001 | ↑ |
| pFKHR-FKHRL1 T24-T32 | 0.0001 | ↑ |
| pIKBa S32 | 0.0341 | ↓ |
| pIKBa S32-36 | 0.0212 | ↓ |
| pmTOR S 2481 | 0.0436 | ↓ |
| pP70 S6 S371 | 0.0006 | ↓ |
| pPDGFR beta Y716 | 0.0262 | ↓ |
| pPDGFRb Y751 | 0.0181 | ↑ |
| pPDK1 S241 | 0.0051 | ↓ |
| pPKC theta T538 | 0.0182 | ↑ |
| pPKC zeta-lambda T410-403 | 0.0001 | ↓ |
| pPKCa S657 | 0.0001 | ↓ |
| pPKCa-b II T638-641 | 0.0017 | ↓ |
| pPRAS40 | 0.0003 | ↑ |
| pPyk2 Y402 | 0.0001 | ↑ |
| pShc Y317 | 0.0001 | ↑ |
| pSMAD2 S465-467 | 0.0043 | ↑ |
| pSrc Y527 | 0.0001 | ↑ |
| pSTAT3 Y705 | 0.0225 | ↓ |
| pSTAT5 Y694 | 0.0159 | ↑ |
| pTEN S380 | 0.0001 | ↓ |
| pVEGFR Y951 | 0.0001 | ↑ |
| pVEGFR2 Y1175 | 0.0481 | ↑ |

Table 3 shows, out of the 80 proteins analyzed, the statistically significant endpoints between primary colorectal cancer and synchronous liver metastases. The right column shows the trend in the hepatic lesions presented in comparison to the primary cancer.

We claim:

1. A method for treating a patient with colorectal cancer that has metastasized to the patient's liver and/or lung comprising the step of administering to the patient a therapeutically effective amount of one or more drugs that target at least two of the following proteins, if two or more of the proteins are found to be elevated in a sample of the metastatic cancer from the patient: pAKT, pSTAT3, pVEGFR, pFKHR-FICHRL1, pcKit, pShc, pSMAD2, pSrc, pSTAT5, pAbl, pJak1, pPyk2, pPDGFRb, pPRAS40, and pEGFR, wherein the drugs are selected from the group consisting of Imatinib mesylate, Bevacizumab, Erlotinib hydrochloride, Panitumumab, Lapatinib, an akt inhibitor, and a PI3 kinase inhibitor.

2. The method of claim 1, wherein the patient's cancer has metastasized to the patient's liver, and the proteins determined to be elevated are at least two of pAbl, pcKit, pPDGFRb, pVEGFR, and pEGFR.

3. The method of claim 2, wherein the selected drug is Imatinib mesylate if pAbl, pcKit, and/or pPDGFRb are elevated, Bevacizumab if pVEGFR is elevated, and Erlotinib hydrochloride, Panitumumab, and/or Lapatinib if pEGFR is elevated.

4. The method of claim 2, wherein the selected drug is Imatinib mesylate if pAbl, pcKit, and/or pPDGFRb are elevated.

5. The method of claim 1, wherein the patient's cancer has metastasized to the patient's lung, and the drug is at least one selected from the group consisting of Imatinib mesylate, Bevacizumab, Erlotinib hydrochloride, Panitumumab, and Lapatinib.

6. The method of claim 1, wherein the proteins are pAKT S473, pSTAT3 S727, pVEGFR Y951 and Y996, pFKHR-FKHRL1 T24-T32, pcKit Y703, pShc Y317, pSMAD2 S465-467, pSrc Y527, pSTAT5 Y694, pAbl Y245, pJak1 Y1022-1023, pPyk2 Y402, pPDGFRb Y751, pPRAS40, and pEGFR Y992 and Y1173.

7. A method for treating a patient with colorectal cancer that has metastasized to the patient's liver and/or lung comprising the step of administering to the patient a therapeutically effective amount of one or more drugs that target at least two of the following proteins, if two or more of the proteins are found to be elevated in a sample of the metastatic cancer from the patient: pAKT S473, pSTAT3 S727, pVEGFR Y951 and Y996, pFKHR-FKHRL1 T24-T32, pcKit Y703, pShc Y317, pSMAD2 S465-467, pSrc Y527, pSTAT5 Y694, pAbl Y245, pJak1 Y1022-1023, pPyk2 Y402, pPDGFRb Y751, pPRAS40, and pEGFR Y992 and Y1173, wherein the drugs are selected from the group consisting of Imatinib mesylate, Bevacizumab, Erlotinib hydrochloride, Panitumumab, Lapatinib, an akt inhibitor, and a PI3 kinase inhibitor.

8. The method of claim 7, wherein the patient's cancer has metastasized to the patient's liver, and the proteins determined to be elevated are at least two of pAbl Y245, pcKit Y703, pPDGFRb Y751, pVEGFR Y951 and Y996, and pEGFR Y992 and Y1173.

9. The method of claim 8, wherein the selected drug is Imatinib mesylate if pAbl Y245, pcKit Y703, and/or pPDGFRb Y751 are elevated, Bevacizumab if pVEGFR Y951 and/or Y996 are elevated, and Erlotinib hydrochloride and/or Lapatinib if pEGFR Y992 and/or Y1173 is elevated.

10. The method of claim 8, wherein the selected drug is Imatinib mesylate if pAbl Y245, pcKit Y703, and/or pPDGFRb Y751 are elevated.

11. The method of claim 7, wherein the patient's cancer has metastasized to the patient's lung, and the drug is at least one selected from the group consisting of Imatinib mesylate, Bevacizumab, Erlotinib hydrochloride, Panitumumab, and Lapatinib.

12. A method of treating a patient with colorectal cancer that has metastasized to the patient's liver comprising the steps of:
(a) determining the combined relative phosphorylation level of Abl, cKit, and PDGFRb in a sample of the patient's metastatic cancer compared to a reference standard; and
(b) administering a therapeutically effective amount of Imatinib mesylate to the patient if the level is above the standard.

13. A method of treating a patient with colorectal cancer that has metastasized to the patient's lung, comprising administering to the patient a therapeutically effective amount of at least one therapeutic selected from the group consisting of Imatinib mesylate, Bevacizumab, Erlotinib hydrochloride, and Lapatinib.

14. A method for treating a patient with colorectal cancer that has metastasized to the patient's liver and/or lung comprising the steps of:
(a) analyzing a sample of the metastatic cancer from the patient to determine if two or more of the following proteins are elevated: pAKT, pSTAT3, pVEGFR, pFKHR-FKHRL1, pcKit, pShc, pSMAD2, pSrc, pSTAT5, pAbl, pJak1, pPyk2, pPDGFRb, pPRAS40, and pEGFR;
(b) selecting one or more drugs for treating the patient that target at least two of any of the proteins found to be elevated, wherein the drugs are selected from the group consisting of Imatinib mesylate, Bevacizumab, Erlotinib hydrochloride, Panitumumab, Lapatinib, an akt inhibitor, and a PI3 kinase inhibitor; and
(c) administering a therapeutically effective amount of the one or more drugs to the patient.

15. The method of claim 14, wherein the step of analyzing the sample comprises:
isolating epithelial cells from the sample;
lysing the epithelial cells; and
analyzing the lysate.

16. The method of claim 15, wherein the cells are isolated by laser capture microdissection and the lysate is distributed onto a reverse phase microarray and then analyzed by an immunoassay.

17. The method of claim 14, wherein the proteins determined to be elevated are at least two of pAKT, pAbl, pcKit, pPDGFRb, pVEGFR, and pEGFR.

18. The method of claim 17, wherein the selected drug is Imatinib mesylate if pAbl, pcKit, and/or pPDGFRb are elevated, Bevacizumab if pVEGFR is elevated, and Erlotinib hydrochloride, and/or Lapatinib if pEGFR is elevated.

19. The method of claim 14, wherein the protein or proteins determined to be elevated are at least two of pAbl, pcKit, and pPDGFRb.

20. The method of claim 19, wherein the selected drug is Imatinib mesylate.

21. The method of claim 14, wherein the proteins are pAKT S473, pSTAT3 S727, pVEGFR Y951 and Y996, pFKHR-FKHRL1 T24-T32, pcKit Y703, pShc Y317, pSMAD2 S465-467, pSrc Y527, pSTAT5 Y694, pAbl Y245, pJak1 Y1022-1023, pPyk2 Y402, pPDGFRb Y751, pPRAS40, and pEGFR Y992 and Y1173.

22. A method for treating a patient with colorectal cancer that has metastasized to the patient's liver and/or lung comprising the steps of:
(a) analyzing a sample of the metastatic cancer from the patient to determine if two or more of the following proteins are elevated: pAKT S473, pSTAT3 S727, pVEGFR Y951 and Y996, pFKHR-FKHRL1 T24-T32, pcKit Y703, pShc Y317, pSMAD2 S465-467, pSrc Y527, pSTAT5 Y694, pAbl Y245, pJak1 Y1022-1023, pPyk2 Y402, pPDGFRb Y751, pPRAS40, and pEGFR Y992 and Y1173;
(b) selecting one or more drugs for treating the patient that target at least two of any of the proteins found to be elevated, wherein the drug is selected from the group consisting of Imatinib mesylate, Bevacizumab, Erlotinib hydrochloride, Panitumumab, Lapatinib, an akt inhibitor, and a PI3 kinase inhibitor; and
(c) administering a therapeutically effective amount of the one or more drugs to the patient.

23. The method of claim 22, wherein the proteins determined to be elevated are at least two of pAKT S473, pAbl Y245, pcKit Y703, pPDGFRb Y751, pVEGFR Y951 and Y996, and pEGFR Y992 and Y1173.

24. The method of claim 23, wherein the selected drug is Imatinib mesylate if pAbl Y245, pcKit Y703, and/or pPDGFRb Y751 are elevated, Bevacizumab if pVEGFR Y951 and/or Y996 is elevated, and Erlotinib hydrochloride and/or Lapatinib if pEGFR Y992 and/or Y1173 is elevated.

25. The method of claim 22, wherein the protein or proteins determined to be elevated are at least two of pAbl Y245, pcKit Y703, and pPDGFRb Y751 and the selected drug is Imatinib mesylate.

26. The method of claim 1, wherein the patient's cancer has metastasized to the patient's liver, and the drug is at least one selected from the group consisting of Imatinib mesylate, Bevacizumab, Erlotinib hydrochloride, Panitumumab, and Lapatinib.

27. The method of claim 7, wherein the patient's cancer has metastasized to the patient's liver, and the drug is at least one selected from the group consisting of Imatinib mesylate, Bevacizumab, Erlotinib hydrochloride, Panitumumab, and Lapatinib.

28. The method of claim 14, wherein the patient's cancer has metastasized to the patient's lung, and the drug is at least one selected from the group consisting of Imatinib mesylate, Bevacizumab, Erlotinib hydrochloride, Panitumumab, and Lapatinib.

29. The method of claim 22, wherein the patient's cancer has metastasized to the patient's lung, and the drug is at least one selected from the group consisting of Imatinib mesylate, Bevacizumab, Erlotinib hydrochloride, Panitumumab, and Lapatinib.

30. The method of claim 14, wherein the patient's cancer has metastasized to the patient's liver, and the drug is at least one selected from the group consisting of Imatinib mesylate, Bevacizumab, Erlotinib hydrochloride, Panitumumab, and Lapatinib.

31. The method of claim 22, wherein the patient's cancer has metastasized to the patient's liver, and the drug is at least one selected from the group consisting of Imatinib mesylate, Bevacizumab, Erlotinib hydrochloride, Panitumumab, and Lapatinib.

* * * * *